United States Patent
Harren et al.

(10) Patent No.: US 7,833,624 B2
(45) Date of Patent: Nov. 16, 2010

(54) ABSORBENT POLYMER STRUCTURE WITH IMPROVED RETENTION CAPACITY AND PERMEABILITY

(75) Inventors: Jörg Harren, Krefeld (DE); Helmut Brehm, Krefeld (DE); Andreas Kerkmann, Goch (DE); Stephan Ramlow, Krefeld (DE)

(73) Assignee: Evonik Stockhuasen GmbH, Krefeld (DE)

( * ) Notice: Subject to any disclaimer, the term of this patent is extended or adjusted under 35 U.S.C. 154(b) by 1431 days.

(21) Appl. No.: 10/532,280

(22) PCT Filed: Oct. 24, 2003

(86) PCT No.: PCT/EP03/11828
§ 371 (c)(1),
(2), (4) Date: Aug. 19, 2005

(87) PCT Pub. No.: WO2004/037903
PCT Pub. Date: May 6, 2004

(65) Prior Publication Data
US 2006/0029782 A1    Feb. 9, 2006

(30) Foreign Application Priority Data
Oct. 25, 2002    (DE) ................. 102 49 821

(51) Int. Cl.
*C08L 33/02* (2006.01)
(52) U.S. Cl. .............. 428/403; 428/404; 428/405; 428/406; 428/407; 525/375; 526/62; 427/212
(58) Field of Classification Search ......... 428/403–407; 525/375; 526/62; 427/212
See application file for complete search history.

(56) References Cited

U.S. PATENT DOCUMENTS

| | | | |
|---|---|---|---|
| 4,535,098 A | | 8/1985 | Evani et al. |
| 4,587,308 A | | 5/1986 | Makita et al. |
| 4,734,478 A | | 3/1988 | Tsubakimoto et al. |
| 5,092,933 A | | 3/1992 | Okamoto et al. |
| 5,140,076 A | * | 8/1992 | Hatsuda et al. ............ 525/375 |
| 5,147,921 A | | 9/1992 | Mallo |
| 5,164,428 A | | 11/1992 | Okamoto et al. |
| 5,229,488 A | | 7/1993 | Nagasuna et al. |
| 5,326,819 A | | 7/1994 | Kanbayashi et al. |
| 5,747,391 A | | 5/1998 | Neubach |
| 5,837,789 A | | 11/1998 | Stockhausen et al. |
| 5,843,575 A | | 12/1998 | Wang et al. |
| 5,849,405 A | | 12/1998 | Wang et al. |
| 5,851,672 A | | 12/1998 | Wang et al. |
| 5,858,535 A | | 1/1999 | Wang et al. |
| 6,056,854 A | | 5/2000 | Woodrum |
| 6,099,950 A | | 8/2000 | Wang et al. |
| 6,232,520 B1 | | 5/2001 | Hird et al. |
| 6,288,158 B1 | | 9/2001 | Schapowalov et al. |
| 6,605,673 B1 | * | 8/2003 | Mertens et al. .......... 525/329.5 |
| 6,620,889 B1 | * | 9/2003 | Mertens et al. ............. 525/221 |
| 6,623,848 B2 | * | 9/2003 | Brehm et al. ................ 428/327 |
| 7,087,669 B2 | | 8/2006 | Ota et al. |
| 7,101,946 B2 | * | 9/2006 | Brehm et al. ............ 526/317.1 |
| 7,179,862 B2 | * | 2/2007 | Mertens et al. ............. 525/221 |
| 2002/0128396 A1 | | 9/2002 | Sackmann et al. |
| 2002/0128618 A1 | | 9/2002 | Frenz et al. |
| 2003/0157318 A1 | | 8/2003 | Brehm et al. |

FOREIGN PATENT DOCUMENTS

| | | |
|---|---|---|
| DE | 3503458 C2 | 8/1985 |
| DE | 3523617 A | 1/1986 |
| DE | 4402187 A1 | 7/1995 |
| DE | 19646484 | 5/1997 |
| DE | 68927772 T2 | 7/1997 |
| DE | 69030971 T2 | 12/1997 |
| DE | 19805447 A1 | 8/1999 |
| DE | 19854575 A1 | 5/2000 |
| DE | 69132818 T2 | 6/2002 |
| EP | 0450922 A | 10/1991 |
| EP | 0450923 A | 10/1991 |
| EP | 1211266 | 6/2002 |

(Continued)

OTHER PUBLICATIONS

Levasil®, The Versatile Silica Sols with a Broad Application Spectrum, copyright Sep. 2006, pp. 1-24, H.C. Starck GmbH & Co. KG.

(Continued)

*Primary Examiner*—Leszek Kiliman
(74) *Attorney, Agent, or Firm*—Smith Moore Leatherwood LLP

(57) ABSTRACT

A process for producing an absorbent polymer structure (Pa) by treating the outer portion of an untreated absorbent polymer structure (Pu1). The process includes the step of bringing the outer portion of the untreated absorbent polymer structure (Pu1) into contact with an aqueous solution including at least one chemical cross-linker and at least one inorganic compound in dispersed colloidal form. The process also includes the step of heating the absorbent polymer structure, of which the outer portion has been brought into contact with the aqueous solution, at a temperature within a range from about 40 to about 300° C., so that the outer portion of the absorbent polymer structure is more strongly cross-linked in comparison to the inner portion and the inorganic compound is at least partly immobilized in the outer portion of the absorbent polymer structure.

18 Claims, No Drawings

FOREIGN PATENT DOCUMENTS

| | | |
|---|---|---|
| EP | 1325777 A1 | 7/2003 |
| JP | H4120176 | 4/1992 |
| JP | 4214734 | 8/1992 |
| JP | H6016822 | 1/1994 |
| JP | 1994-16822 | 8/1995 |
| JP | 9194598 | 7/1997 |
| JP | 2001137704 | 5/2001 |
| WO | WO 95/22356 | 8/1995 |
| WO | WO 99/49905 | 10/1999 |
| WO | WO 01/13841 | 3/2001 |
| WO | 0166056 | 9/2001 |
| WO | 0205949 A1 | 1/2002 |
| WO | 0220678 A1 | 3/2002 |

OTHER PUBLICATIONS

Nissan Chemical America Corporation, SNOWTEX Information Sheet, copyright 2007, web site, www.nissanchem-usa.com/snowtex.php, Nissan Chemical America Corporation.

International Preliminary Examination Report completed on Jul. 16, 2004 in connection with PCT/EP2003/011828.

* cited by examiner

ABSORBENT POLYMER STRUCTURE WITH IMPROVED RETENTION CAPACITY AND PERMEABILITY

This application is a national stage application under 35 U.S.C. 371 of international application no. PCT/EP2003/011828 filed Oct. 24, 2003, which is based on German Application No. DE 102 49 821.0, filed Oct. 25, 2002, and claims priority thereto.

BACKGROUND OF THE INVENTION

The invention is related to a process for producing an absorbent polymer structure, an absorbent polymer structure obtainable by this process, an absorbent polymer structure, a compound, a process for producing a compound, a compound obtainable by this process, chemical products comprising the absorbent polymer structure or the compound, the use of the absorbent polymer structure or the compound in chemical products, an aqueous solution, a process for producing the aqueous solution, an aqueous solution obtainable by the process as well as the use of the aqueous solution in treatment of the outer portion of an absorbent polymer structure.

Superabsorbers are water insoluble cross-linked polymers, which are capable, by swelling and formation of hydrogels, of absorbing large quantities of aqueous liquids, in particular body liquids, preferably urine or blood, and retaining them under a certain pressure. Because of these characteristic properties these polymers find applications mainly through incorporation into sanitary articles, such as, for example, baby diapers, incontinence products or sanitary napkins.

Existing commercially available superabsorbers are essentially made up of cross-linked polyacrylic acids or cross-linked starch-acrylic acid graft polymerizates, in which the carboxyl groups are partly neutralized with sodium hydroxide or potassium hydroxide.

For aesthetic reasons and on environmental grounds there is an increasing tendency to create ever smaller and thinner sanitary articles. In order to ensure a consistent overall retention capacity of the sanitary article, this demand can only be met through reduction of the proportion of voluminous fluff. This means that further tasks fall to the superabsorber with respect to transport and distribution of liquids, which can be summarised as permeability properties.

By permeability in superabsorbent materials is understood the ability, in the swollen state, to transport and distribute added liquids in three dimensions. This process proceeds in the swollen superabsorbent gel via capillary transport through gaps between the gel particles. Liquid transport through swollen superabsorber particles themselves follows the laws of diffusion and is a very slow process, which plays no role in the distribution of the liquid in the utilization situation of the sanitary article. For superabsorbent materials that cannot accomplish capillary transport for reasons of lack of gel stability, a separation of the particles from each other to prevent the gel-blocking phenomenon was ensured by embedding these materials in a fiber matrix. In newer generations of diaper constructions the absorbent layer contains only little or indeed no fibrous material at all to support liquid transport. Superabsorbers used here must thus possess a sufficiently high stability in the swollen state such that the swollen gel still contains a sufficient quantity of capillary spaces, through which the liquid can be transported.

In order to obtain superabsorbent materials with higher gel stability, on the one hand the degree of cross-linking of the polymer can be increased, which inevitably results in a decrease of the swelling ability and the retention capacity. An optimized combination of different cross-linkers and co-monomers, as described in DE 196 46 484, does enable the improvement of the permeability properties, but not to a level which permits for example the fitting of a layer composed optionally of only superabsorbers into a diaper construction.

Furthermore, methods for secondary treatment of the surface of polymer particles to improve the superabsorbent properties can be applied. As surface treatment are known from prior art for example secondary cross-linking of the absorbent polymer structure at the surface, the bringing into contact of the surface with inorganic compounds or the secondary cross-linking of the surface in the presence of inorganic compounds.

Thus EP-A-0 450 923, EP-A-0 450 922, DE-A-35 23 617, U.S. Pat. No. 5,140,076 and U.S. Pat. No. 4,734,478 describe the treatment of the surface of absorbent polymers by bringing the surface into contact with inorganic compounds, such as for example dispersed silica, during or after the secondary cross-linking of the surface. Next to an increased rate of absorption under pressure an increased permeability of the absorbent polymer is also achieved by this type of surface treatment.

DE 35 03 458 describes a process for producing an improved absorbent resin, wherein a water absorbent resin, which contains units of a monomer, said monomer having a carboxyl group in the form of the free acid or of a salt, as a constituent component of the resin, in the presence of a powder of a finely divided metal oxide, permits the absorption of a cross-linking medium and water and the resulting mixture is heated while agitating, in order to effect the cross-linking of the resin and the removal of the water. Absorbent resins with a good water absorption capacity are obtained hereby, which at the same time have a good rate of absorption.

U.S. Pat. No. 4,535,098 describes a process for increasing the gel strength of non-secondary cross-linked superabsorbers by swelling of absorbent polymers in the presence of a dispersed colloidal inorganic compound, such as a silica sol, or by producing an absorbent polymer in the presence of a dispersed colloidal inorganic compound.

DE 198 05 447 discloses a process for secondary cross-linking of polyacrylonitrile hydrolysates with bifunctional compounds and a simultaneous immobilization of silica in the surface structure of superabsorbent polymers. The silica together with the cross-linking medium in a water/alcohol mixture was brought into contact with the surface. By immobilizing the silica an improvement of the Absorbency under Load as well as a decrease in gel blocking should be achieved.

DE 198 54 575 describes the addition of alkali salts of silicic acid before, during or after the polymerization or in partial neutralization of the superabsorber. Through this surface treatment an improved permeability is achieved, which is however principally ascribed to the partially reduced retention of the polymers caused by non-swellable additive.

U.S. Pat. No. 5,147,921 discloses the addition of a silica sol as inert filler, which can be dispersed in the monomer solution to be polymerized.

JP 1994-16822 describes the secondary treatment of the surface of absorbent polymers with an inorganic sol. In the context of the processability of the mixture, which tends to form agglomerates, an additional organic solvent component is added. Mono- and dimethylethers of diols or diols themselves are cited as examples of organic solvent components. After drying the absorbent polymers should have higher gel stability, a reduced tendency to gel blocking and an improved permeability to water in simple tests without pressure stress on the superabsorber.

The prior art describes processes by which inorganic particles are either dry blended with the superabsorber or introduced into the secondary cross-linking process with the aid of a large quantity of in part organic solvent, in order to prevent an agglomeration of the superabsorber particles. These processes present however the disadvantage, that either large quantities of solvents must be handled, which is as undesirable on economic as it is on ecological grounds. Furthermore superabsorbent polymers tend to agglomerate when mixed with large quantities of liquids, which can seriously impair the processability within a continual production process. A simple blend with inorganic finely divided substances on the other hand leads to disadvantages, such as decomposition or dust. The addition of inorganic additives in aqueous solutions to the cross-linking itself is difficult, since the inorganic particles are quickly deposited. Moreover, it can be difficult to dose accurately inorganic dispersions.

Partly through the presence of the finely divided inorganic substances disclosed in the prior art, an inhomogeneous distribution of the chemical secondary cross-linkers occurs on the surface of the absorbent polymers and accordingly also an inhomogeneous cross-linking. This in turn leads to superabsorbent polymers being obtained with a dissatisfactory overall performance, above all with respect to retention and permeability. A homogeneous distribution in the surface treatment processes in the prior art is in all cases possible by using large quantities of an aqueous or alcoholic solution containing the chemical cross-linker.

The general objects underlying the present invention are to overcome the drawbacks arising from the state of the art.

Furthermore, an object according to the invention consists in making available superabsorbent polymers which unite as a combination of properties not only a high absorption capacity under pressure but also the typically opposing properties of a high retention capability and a good permeability, in order to satisfy the demands on absorbent polymers of modern hygiene articles, in particular diapers, incontinence products or sanitary napkins. In particular these polymers should comprise the smallest possible quantities of toxic monomers, such as acrylamide or acrylonitrile, which are washed out upon a contact of the superabsorbent polymer with body liquids and, for example in the case of the use of the superabsorbent polymers in diapers, could in this way come into contact with the skin of the person wearing the diaper.

A further object underlying the present invention consisted in the provision of hygiene articles such as for example diapers, which in comparison to the hygiene articles known from the state of the art are better able to retain absorbed body liquids, to absorb liquids under pressure, and, on absorbing liquids, to distribute these liquids as quickly and evenly as possible in the hygiene article.

In addition, another object according to the invention lies in the creation of a process with which such absorbent polymers can be produced with the smallest possible quantities of organic solvents. In this production process added inorganic additives should displace superabsorbent polymer at most in small amounts, which do not negatively influence the polymer properties. The solution employed in this process for treatment of the surface of the absorbent polymer should be able to be handled as a single-phase system and be consistently dosed. The coated superabsorber should form aggregates to only a slight extent in the course of the process and should be able to be applied simply to a continuously operating tempering step.

DETAILED DESCRIPTION OF THE INVENTION

The above objects are achieved through a process for producing an absorbent polymer structure (Pa) by treating the outer portion of an untreated polymer structure (Pu1), including the steps of:
bringing the outer portion of the untreated absorbent polymer structure (Pu1) into contact with an aqueous solution containing at least one chemical cross-linker and at least one inorganic compound in dispersed colloidal form; and
heating the absorbent polymer structure, of which the outer portion has been brought into contact with the aqueous solution, at a temperature in the range from about 40 to about 300° C., so that, preferably in this way, the outer portion of the absorbent polymer structure is more strongly cross-linked compared to the inner portion and the inorganic compound is at least partly immobilized in the outer portion of the absorbent polymer structure.

The above objects are also achieved through a process for producing an absorbent polymer structure (Pa) by treating the outer portion of an absorbent polymer structure (Pu2), that has not been treated with an inorganic compound in dispersed colloidal form, including the steps of:
bringing the outer portion of the absorbent polymer structure (Pu2) into contact with an aqueous solution containing at least one chemical cross-linker and at least one inorganic compound in dispersed colloidal form; and
heating the absorbent polymer structure, of which the outer portion has been brought into contact with the aqueous solution, at a temperature in the range from about 40 to about 300° C., so that, preferably in this way, the outer portion of the absorbent polymer structure is more strongly cross-linked compared to the inner portion and the inorganic compound is at least partly immobilized in the outer portion of the absorbent polymer structure.

Absorbent polymer structures (Pa) according to the invention are fibers, foams or particles, wherein fibers and particles are preferred and particles particularly preferred. Absorbent polymer structures (Pa) in these forms are obtained, by using fibers, foams or particles as absorbent polymer structure (Pu1) or (Pu2) correspondingly.

Preferred absorbent polymer fibers according to the invention are so dimensioned, that they can be worked into or as yarns for textiles and also directly into textiles. According to the invention it is preferred that the absorbent polymer fibers possess a length in the range from about 1 to about 500, preferably about 2 to about 500 and particularly preferably about 5 to about 100 mm and a diameter in the range from about 1 to about 200, preferably about 3 to about 100 and particularly preferably about 5 to about 60 denier.

Preferred absorbent polymer particles according to the invention are so dimensioned, that they have an average particle size according to ERT 420.1-99 in the range from about 10 to about 3000, preferably about 20 to about 2000 and particularly preferably about 150 to about 850 μm.

The absorbent polymer structure (Pu1) or (Pu2) in processes according to the invention is preferably a polymer structure, which is based on:
(α1) about 20 to about 99.999 wt. %, preferably about 55 to about 98.99 wt. % and particularly preferably about 70 to about 98.79 wt. % of polymerized, ethylenically unsaturated, acidic group-containing monomers or salts thereof or polymerized, ethylenically unsaturated, protonated or quaternary nitrogen-containing monomer, or mixtures thereof, wherein at least ethylenically unsaturated, acidic group-containing monomers, preferably acrylic acid, comprising mixtures are particularly preferred, (α2) 0 to about 80 wt. %, preferably 0 to about 44.99 wt. % and particularly preferably about 0.1 to about 44.89 wt. % polymerized, monoethylenically unsaturated monomers which are copolymerizable with (α1), (α3) about 0.001 to about 5 wt. %, preferably about 0.01 to about 3 wt. % and particularly preferably about 0.01 to about 2.5 wt. % of one or more cross-linkers, (α4) 0 to about 30 wt. %, preferably 0 to about 5 wt. % and particularly preferably about 0.1 to about 5 wt. % of a water soluble polymer, as well as (α5) 0 to about 20 wt. %, preferably 0 to about 10 wt. % and particularly preferably about 0.1 to about 8 wt. % of one or more additives, whereby the sum of the component weights (α1) to (α5) amounts to 100 wt. %.

The monoethylenically unsaturated, acidic group-containing monomers (α1) can be partially or fully neutralized. The monoethylenically unsaturated, acidic group-containing monomers are preferably about 25 mol %, particularly preferably about 50 mol % and even more preferably about 50 to about 80 mol % neutralized. In this context DE 195 29 348 is referred to. The neutralization can also partly or wholly take place after the polymerization. Furthermore, the neutralisation can occur with alkali metal hydroxides, alkaline earth metal hydroxides, ammonia as well as carbonates and bicarbonates. Any further base which forms a water soluble salt with the acid is also conceivable. A mixed neutralisation with several bases is also conceivable. Neutralization with ammonia and alkali metal hydroxides is preferred, with sodium hydroxide and with ammonia is particularly preferred.

Furthermore the free acidic groups can predominate in a polymer, so that this polymer has a pH value lying in the acidic region. This acidic water-absorbing polymer can be at least partially neutralized by a polymer with free basic groups, preferably amino groups, which polymer is basic in comparison to the acidic polymer. These polymers are described in the literature as "Mixed-Bed Ion-Exchange Absorbent Polymers" (MBIEA-polymers) and are disclosed in WO 99/34843 among others. As a rule MBIEA-polymers produce a compound which comprises on the one hand basic polymers, which are in a position to exchange anions and on the other hand a polymer which is acidic in comparison to the basic polymer, said acidic polymer being in a position to exchange cations. The basic polymer has basic groups and is typically obtained by polymerization of monomers which carry basic groups or groups which can be converted into basic groups. With these monomers it is above all else a matter of those which have primary, secondary or tertiary amines or the corresponding phosphines or at least two of the above functional groups. To this group of monomers belong particularly ethylenamine, allylamine, diallylamine, 4-aminobutene, alkyloxycycline, vinylformamide, 5-aminopentene, carbodiimide, formaldacine, melamine and the like, as well as secondary or tertiary amine derivatives thereof.

The monoethylenically unsaturated, acidic group-containing monomers (α1) can be partly or fully, preferably partly neutralized. The monoethylenically unsaturated acidic groups are neutralized preferably to at least about 25 mol %, particularly preferably to at least about 50 mol % and above all preferably about 50 to about 90 mol %. The neutralization of the monomers (α1) can occur before and also after the polymerization. Furthermore, the neutralisation can be carried out with alkali metal hydroxides, alkaline earth metal hydroxides, ammonia, as well as carbonates and bicarbonates. In addition any further base which forms a water soluble salt with the acid is conceivable. A mixed neutralization with different bases is also conceivable. Neutralization with ammonia or with alkali metal hydroxides is preferred, with sodium hydroxide or with ammonia is particularly preferred.

Preferred monoethylenically unsaturated, acidic group-containing monomers (α1) are acrylic acid, methacrylic acid, ethacrylic acid, α-chloroacrylic acid, α-cyanoacrylic acid, β-methylacrylic acid (crotonic acid), α-phenylacrylic acid, β-acryloxypropionic acid, sorbinic acid, α-chlorosorbinic acid, 2'-methylisocrotonic acid, cinnamic acid, p-chlorocinnamic acid, β-stearic acid, itaconic acid, citraconic acid, mesaconic acid, glutaconic acid, aconitic acid, maleic acid, fumaric acid, tricarboxythylene and maleic acid anhydride, where acrylic acid and methacrylic acid and above all acrylic acid are particularly preferred.

Besides these carboxylate group-containing monomers, further preferred monoethylenically unsaturated acidic group-containing monomers (α1) are ethylenically unsaturated sulfonic acid monomers or ethylenically unsaturated phosphonic acid monomers.

Preferred ethylenically unsaturated sulfonic acid monomers are allylsulfonic acid or aliphatic or aromatic vinylsulfonic acids or acrylic or methacrylic acids. Preferred aliphatic or aromatic vinylsulfonic acids are vinylsulfonic acid, 4-vinylbenzylsulfonic acid, vinyltoluenesulfonic acid and styrenesulfonic acid. Preferred acrylic or methylacrylic acids are sulfoethyl(meth)acrylate, sulfopropyl(meth)acrylate, 2-hydroxy-3-methacryloxypropylsulfonic acid and 2-acrylamido-2-methylpropansulfonic acid.

Additionally preferred are ethylenically unsaturated phosphonic acid monomers, such as vinylphosphonic acid, allylphosphonic acid, vinylbenzylphosphonic acid, (meth)acrylamidoalkylphosphonic acids, acrylamidoalkyldiphosphonic acids, phosphonomethylated vinylamines and (meth)acrylphosphonic acid derivatives.

Preferred ethylenically unsaturated monomers (α1) containing a protonated nitrogen are preferentially dialkylaminoethyl(meth)acrylate-hydrochlorides in the protonated form, for example dimethylaminoethyl(meth)acrylate-hydrochloride or dimethylaminoethyl(meth)acrylate-hydrosulfate, as well as dialkylaminoalkyl(meth)acrylamides in the protonated form, for example dimethylaminoethyl(meth)acrylamide-hydrochloride or dimethylaminoethyl(meth)acrylamide-hydrosulfate.

Preferred ethylenically unsaturated monomers (α1) containing a quaternated nitrogen are dialkylammoniumalkyl(meth)acrylates in quaternated form, for example trimethylammoniumethyl(meth)acrylate-methosulfate or dimethylethylammoniumethyl(meth)acrylate-ethosulfate as well as (meth)acrylamidoalkyldialkylamine in quaternated form, for example (meth)acrylamidopropyltrimethylammonium chloride and (meth)acrylamidopropyltrimethylammonium sulfate.

According to the invention it is preferred that the component (α1) comprises at least about 50 wt. %, preferably at least about 70 wt. % and more preferably at least about 90 wt. % carboxylate group-containing monomers. According to the invention it is particularly preferred that the component (α1) comprises at least about 50 wt. %, preferably at least about 70 wt. % acrylic acid, which is neutralized preferably to at least about 20 mol % and particularly preferably to at least about 50 mol %.

Preferred monoethylenically unsaturated monomers (α2) which can be co-polymerized with (α1) are acrylamides and (meth)acrylamides.

Possible (meth)acrylamides besides acrylamide and methacrylamide are alkyl-substituted (meth)acrylamides or aminoalkylsubstituted derivatives of (meth)acrylamides such as N-methylol(meth)acrylamide, N,N-dimethylamino(meth)acrylamide, dimethyl(meth)acrylamide or diethyl(meth)acrylamide. Possible vinylamides are for example N-vinylamides, N-vinylformamides, N-vinylacetamides, N-vinyl-N-methylacetamide, N-vinyl-N-methylformamides, vinylpyrrolidone. Among these monomers acrylamide is particularly preferred.

Further preferred monoethylenically unsaturated monomers (α2) which are copolymerizable with (α1) are water-dispersible monomers. Preferred water-dispersible monomers are acrylic acid esters and methycrylic acid esters, such as methyl(meth)acrylate, ethyl(meth)acrylate, propyl(meth)acrylate or butyl(meth)acrylate, as well as methylpolyethyleneglycol(meth)acrylate, methylpolyethyleneglycolallylether, vinylacetate, styrene and isobutylene.

Preferred cross-linkers (α3) according to the invention are compounds which have at least two ethylenically unsaturated groups in one molecule (cross-linker class I), compounds which have at least two functional groups which can react with functional groups of the monomers (α1) or (α2) in a condensation reaction (=condensation cross-linkers), an addition reaction or a ring-opening reaction (cross-linker class II), compounds which have at least one ethylenically unsaturated group and at least one functional group which can react with functional groups of the monomers (α1) or (α2) in a condensation reaction, an addition reaction or a ring-opening reaction (cross-linker class III), or polyvalent metal cations (cross-linker class (IV). Thereby a cross-linking of the polymer is achieved with the compounds of cross-linker class I by radical polymerization or the ethylenically unsaturated groups of the cross-linker molecules with the monoethylenically unsaturated monomers (α1) or (α2), while with the compounds of cross-linker class II and the polyvalent metal cations of cross-linker class IV a cross-linking of the polymer is achieved via condensation reaction of the functional groups (cross-linker class II) or via electrostatic interaction of the polyvalent metal cation (cross-linker class IV) with the functional groups of the monomer (α1) or (α2). With compounds of cross-linker class III a cross-linking of the polymers is achieved correspondingly by radical polymerization of the ethylenically unsaturated groups or just as well by condensation reaction between the functional groups of the cross-linkers and the functional groups of the monomers (α1) or (α2).

Preferred compounds of cross-linker class I are poly(meth)acrylic acid esters or poly(meth)acrylamides, which have been obtained for example by conversion of a polyol, such as for example ethylene glycol, propylene glycol, trimethylolpropane, 1,6-hexanediol, glycerin, pentaerythritol, polyethyleneglycol or polypropyleneglycol, of an aminoalcohol, a polyalkylenepolyamine, such as for example diethylenetriamine or triethylenetetraamine, or of an alkoxidised polyol with acrylic acid or methacrylic acid. Further preferred compounds of cross-linker class I are polyvinyl compounds, poly(meth)allyl compounds, (meth)acrylic acid esters of a monovinyl compound or (meth)acrylic acid esters of a mono (meth)allyl compound, preferably of the mono(meth)allyl compounds of a polyol or of an aminoalcohol. In this context DE 195 43 366 and DE 195 43 368 are referred to.

As examples of compounds of cross-linker class I are named alkenyldi(meth)acrylates, for example ethyleneglycoldi(meth)acrylate, 1,3-propyleneglycoldi(meth)acrylate, 1,4-butyleneglycoldi(meth)acrylate, 1,3-butyleneglycoldi(meth)acrylate, 1,6-hexanedioldi(meth)acrylate, 1,10-decanedioldi(meth)acrylate, 1,12-dodecanedioldi(meth)acrylate, 1,18-octadecanedioldi(meth)acrylate, cyclopentanedioldi(meth)acrylate, neopentylglycoldi(meth)acrylate, methylenedi(meth)acrylate or pentaerythritoldi(meth)acrylate, alkenyldi(meth)acrylamides, for example N-methyldi(meth)acrylamide, N,N'-3-methylbutylidenebis(meth)acrylamide, N,N'-(1,2-dihydroxyethylene)bis(meth)acrylamide, N,N'-hexamethylenebis(meth)acrylamide or N,N'-methylenebis(meth)acrylamide, polyalkoxydi(meth)acrylates, for example diethyleneglycoldi(meth)acrylate, triethyleneglycoldi(meth)acrylate, tetraethyleneglycoldi(meth)acrylate, dipropyleneglycoldi(meth)acrylate, tripropyleneglycoldi(meth)acrylate or tetrapropyleneglycoldi(meth)acrylate, bisphenol-A-di(meth)acrylate, ethoxylated bisphenol-A-di(meth)acrylate, benzylidenedi(meth)acrylate, 1,3-di(meth)acryloyloxypropanol-2, hydroquinonedi(meth)acrylate, di(meth)acrylate esters of trimethylolpropane, which are preferably alkoxylated with 1 to 30 mol alkylene oxide per hydroxyl group, preferably ethoxylated trimethylolpropane, thioethyleneglycoldi(meth)acrylate, thiopropyleneglycoldi(meth)acrylate, thiopolyethyleneglycoldi(meth)acrylate, thiopolypropyleneglycoldi(meth)acrylate, divinyl ethers, for example 1,4-butanedioldivinylether, divinyl esters, for example divinyladipate, alkanedienes, for example butadiene or 1,6-hexadiene, divinylbenzene, di(meth)allyl compounds, for example di(meth)allylphthalate or di(meth)allylsuccinate, homo- and co-polymers of di(meth)allyldimethylammonium chloride and homo- and co-polymers of diethyl(meth)allylaminomethyl(meth)acrylateammonium chloride, vinyl(meth)acrylic compounds, for example vinyl(meth)acrylate, (meth)allyl(meth)acrylic compounds, for example (meth)allyl(meth)acrylate, (meth)allyl(meth)acrylate ethoxylated with about 1 to about 30 mol ethylene oxide per hydroxyl group, di(meth)allylesters of polycarbonic acids, for example di(meth)allylmaleate, di(meth)allylfumarate, di(meth)allylsuccinate or di(meth)allylterephthalate, compounds with 3 or more ethylenically unsaturated, radically polymerizable groups such as for example glycerine tri(meth)acrylate, (meth)acrylate esters of glycerins ethoxylated with preferably 1 to 30 mol ethylene oxide per hydroxyl group, trimethylolpropanetri(meth)acrylate, tri(meth)acrylate esters of trimethylolpropane which is alkoxylated preferably with about 1 to about 30 mol alkylene oxide per hydroxide group, preferably ethoxylated trimethylolpropane, trimethacrylamide, (meth)allylidenedi(meth)acrylate, 3-allyloxy-1,2-propanedioldi(meth)acrylate, tri(meth)allylcyanurate, tri(meth)allylisocyanurate, pentaerythritoltetraa(meth)acrylate, pentaerythritoltri(meth)acrylate, (meth)acrylic acid esters of pentaerythritol which is ethoxylated with preferably about 1 to about 30 mol ethylene oxide per hydroxyl group, tris(2-hydroxyethyl)isocyanuratetri(meth)acrylate, trivinyltrimellitate, tri(meth)allylamine, di(meth)allylalkylamines, for example di(meth)allylmethylamine, tri(meth)allylphosphate, tetra(meth)allylethylenediamine, poly(meth)allyl ester, tetra(meth)allyloxyethane or tetra(meth)allylammonium halides.

Preferred compounds of cross-linker class II are compounds which have at least two functional groups which can react with the functional groups of the monomers (α1) or (α2), preferably with acidic groups of the monomers (α1), in a condensation reaction (=condensation cross-linkers), in an addition reaction or in a ring opening reaction. Examples of these functional groups of the compounds of cross-linker class II can be alcoholic, amino, aldehyde, glycidic, isocyanate, carbonate or epichloro functions.

As examples of compounds of cross-linker class II are mentioned polyols, for example ethyleneglycol, polyethyleneglycols such as diethyleneglycol, triethyleneglycol and tetraethyleneglycol, propyleneglycol, polypropyleneglycols such as dipropyleneglycol, tripropyleneglycol or tetrapropyleneglycol, 1,3-butanediol, 1,4-butanediol, 1,5-pentanediol, 2,4-pentanediol, 1,6-hexanediol, 2,5-hexanediol, glycerine, polyglycerin, trimethylolpropane, polyoxypropylene, oxyethylene-oxypropylene-block copolymer, sorbitan-fatty acid esters, polyoxyethylenesorbitan-fatty acid esters, pentaerythritol, polyvinylalcohol and sorbitol, aminoalcohols, for example ethanolamine, diethanolamine, triethanolamine or propanolamine, polyamine compounds, for example ethylenediamine, diethylenetriamine, triethylenetetraamine, tetraethylenepentaamine or pentaethylenehexaamine, polyglycidyl ether compounds such as ethyleneglycoldiglycidyl ether, polyethyleneglycoldiglycidyl ether, glycerinediglycidyl ether, glycerinepolyglycidyl ether, pentaerithritolpolyglycidyl ether, propyleneglycoldiglycidyl ether, polypropyleneglycoldiglycidyl ether, neopentylglycoldiglycidyl ether, hexanediolglycidyl ether, trimethylolpropanepolyglycidyl ether, sorbitolpolyglycidyl ether, phthalic acid diglycidyl ester, adipinic acid diglycidyl ether, 1,4-phenylenebis(2-oxazoline), glycidol, polyisocyanates, preferably diisocyanates such as 2,4-toluenediioscyanate and hexamethylenediisocyanate, polyaziridine compounds such as 2,2-bishydroxymethylbutanol-tris[3-(1-aziridinyl)propionate], 1,6-hexamethylenediethyleneurea and diphenylmethane-bis-4,4'-N,N'-diethyleneurea, halogen epoxides for example epichloro- and epibromohydrin and α-methylepichlorohydrin, alkylenecarbonates such as 1,3-dioxolane-2-one (ethylene carbonate), 4-methyl-1,3-dioxolane-2-one (propylene carbonate), 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, 1,3-dioxolane-2-one, poly-1,3-dioxolane-2-on, polyquaternary amines such as condensation products from dimethylamines and epichlorohydrin. Further preferred compounds of the cross-linker class II are in addition polyoxazolines such as 1,2-ethylenebisoxazoline, cross-linkers with silane groups such as γ-glycidooxypropyltrimethoxysilane and γ-aminopropyltrimethoxysilane, oxazolidinones such as 2-oxazolidinone, bis- and poly-2-oxazolidinone and diglycolsilicates.

Preferred compounds of class III are hydroxyl or amino group-containing esters of (meth)acrylic acid, such as for example 2-hydroxyethyl(meth)acrylate, as well as hydroxyl or amino group-containing (meth)acrylamides, or mono (meth)allylic compounds of diols.

The polyvalent metal cations of the cross-linker class IV are derived preferably from singly or multiply charged cations, the singly charged in particular from alkali metals such as potassium, sodium, lithium, wherein lithium is preferred. Preferred doubly charged cations are derived from zinc, beryllium, alkaline earth metals such as magnesium, calcium, strontium, wherein magnesium is preferred. Further cations applicable according to the invention with higher charge are cations from aluminium, iron, chromium, manganese, titanium, zirconium and other transition metals as well as double salts of such cations or mixtures of the named salts. The use of aluminium salts and alums and various hydrates thereof such as e.g. $AlCl_3 \times 6\ H_2O$, $NaAl(SO_4)_2 \times 12\ H_2O$, $KAl(SO_4)_2 \times 12\ H_2O$ or $Al_2(SO_4)_3 \times 14\text{-}18 H_2O$ is preferred.

The use of $Al_2(SO_4)_3$ and its hydrates as cross-linkers of the cross-linker class IV is particularly preferred.

Preferred absorbent polymer structures (Pu1) or (Pu2) are polymer structures, which are cross-linked by cross-linkers of the following cross-linker classes or by cross-linkers of the following combinations of cross-linker classes: I, II, III, IV, I II, I III, I IV, I II III, I II IV, I III IV, II III IV, II IV or III IV. The above combinations of cross-linker classes produce respectively a preferred embodiment of cross-linkers of a polymer.

Further preferred embodiments of the absorbent polymer structures (Pu1) or (Pu2) are polymer structures, which are cross-linked by any of the above named cross-linkers of cross-linker class I. Among these, water soluble cross-linkers are preferred. In this context, N,N'-methylenebisacrylamide, polyethyleneglycoldi(meth)acrylate, triallylmethylammonium chloride, tetraallylammonium chloride as well as allylnonaethyleneglycolacrylate made with 9 mol ethylene oxide per mol acrylic acid are particularly preferred.

As water soluble polymers (α4), water soluble polymerizates such as those comprising partly or fully saponified polyvinyl alcohol, polyvinylpyrrolidone, starches or starch derivatives, polyglycols or polyacrylic acids can preferably be polymerized into the absorbent polymer structures (Pu1) or (Pu2) according to the invention. The molecular weight of these polymers is not critical, as long as they are water soluble. Preferred water soluble polymers are starches or starch derivatives or polyvinyl alcohol. The water soluble polymers, preferably synthetic like polyvinyl alcohol, can also serve as graft basis for the monomers to be polymerized.

As additives (α5), suspension agents, surface-active agents, odour binders, filling material or antioxidants can preferably be contained in the absorbent polymer structure (Pu1) or (Pu2) used in the process according to the invention.

According to the invention it is particularly preferred, that the absorbent polymer structure (Pu1) or (Pu2) is a cross-linked polyacrylate in particulate form, which was obtained by polymerization of an acrylic acid and optionally of one of the above mentioned cross-linkers in aqueous solution, comprising the acrylic acid in a quantity within a range from about 5 to about 80 wt. %, preferably about 10 to about 70 wt. % and particularly preferably about 20 to about 50 wt. %, based on the weight of the aqueous solution, and then reducing to small pieces the obtained polymer gel, drying the gel which has been reduced to small pieces and optionally further grinding of the dried polymer gel. Absorbent polymer structures obtained in this manner are preferably characterized by a water content of about 0.5 to about 25 wt. %, preferably of about 1 to about 10 wt. %.

In a preferred embodiment of the present invention, the absorbent polymer structure (Pu1) or (Pu2) is neutralized to at least about 50 wt. %, preferably to at least about 75 wt. % and above all preferably to at least about 90 wt. % based on acrylic acid, which is preferably neutralized to at least about 20 mol %, particularly preferably to at least about 50 mol %.

It is further preferred, that the absorbent polymer structure (Pu1) or (Pu2) is not based on polyacrylonitrile emulsions. Therein it is preferred, that the absorbent polymer structure (Pu1) or (Pu2) is based on less than about 37 mol %, particularly preferred on less than about 20 mol %, further preferred on less than about 10 mol % and even more preferred on less than about 5 mol % of acrylamide and/or acrylonitrile monomers. In this context it is furthermore preferred, that the absorbent polymer structure (Pu1) or (Pu2) has a proportion of soluble monomers or polymers based on acrylonitrile and/ or acrylamide monomers of less than about 1000 ppm, particularly preferred of less than about 500 ppm, further preferred of less than about 100 ppm and even more preferred of less than about 10 ppm.

The absorbent polymer structure (Pu1) or (Pu2) can be produced from the above-named monomers and cross-linkers by various polymerization means. For example, in this context can be named bulk polymerization which occurs preferably in kneading reactors such as extruders, solution polymerization, spray polymerization, inverse emulsion polymerization and inverse suspension polymerization. Solution polymerization is preferably carried out in water as solvent. The solution polymerization can occur continuously or discontinuously. From the prior art a broad spectrum of variation possibilities can be gathered with respect to reaction proportions such as temperature, type and quantity of the initiators as well as of the reaction solution. Typical processes are described in the following patent specifications: U.S. Pat. No. 4,286,082, DE 27 06 135, U.S. Pat. No. 4,076,663, DE 35 03 458, DE 40 20 780, DE 42 44 548, DE 43 23 001, DE 43 33 056, DE 44 18 818.

Another possibility for producing the absorbent polymer structure (Pu1) or (Pu2) is to first produce non-cross-linked, in particular linear polymers, preferably by radical means from the above named monoethylenically unsaturated monomers ($\alpha 1$) or ($\alpha 2$) and then to convert these with reagents acting as a cross-linker ($\alpha 3$), preferably with those of classes II and IV. This variant is then used preferentially if the polymer structure should be first processed in form-giving processes, for example to form fibers, films or other flat structures such as fabrics, knitted fabrics, webs or fleeces, and cross-linked in this form.

The polymerization is initiated by an initiator as is generally customary. All initiators forming radicals under the polymerization conditions can be used as initiators for the initiation of the polymerization, which initiators are customarily used in production superabsorbers. An initiation of the polymerization by action of electron beams on the polymerizable aqueous solution is also possible. The polymerization can indeed be initiated in the absence of initiators of the above-mentioned type by action of energetic beams in the presence of photo-initiators. Polymerization initiators can be used dissolved or dispersed in a solution of monomer according to the invention. All compounds known to one experienced in the art to decompose into radicals can be used as initiators. Hereunder fall in particular peroxides, hydroperoxides, hydrogen peroxide, persulfates, azo compounds as well as the so-called redox catalysts. Preferred is the use of water soluble catalysts. In some cases it is advantageous to use mixtures of different polymerization initiators. Among these mixtures are preferred those comprising hydrogen peroxide and sodium or potassium peroxodisulfate, which can be used in any conceivable quantity ratio. Suitable organic peroxides are preferably acetylacetone peroxide, methylethylketone peroxide, t-butylhydroperoxide, cumolhydroperoxide, t-amylperpivalate, t-butylperpivalate, t-butylpemeohexonate, t-butylisobutyrate, t-butylper-2-ethylhexenoate, t-butylperisononanoate, t-butylpermaleate, t-butylperbenzoate, t-butyl-3,5,5-trimethylhexanoate and amylperneodecanoate. Additionally preferred as polymerization initiators are: azo compounds, such as 2,2'-azobis(2-amidinopropane)-dihydrochloride, azobisamidinopropane-dihydrochloride, 2,2'-azobis(N,N-dimethylene)isobutyramidine-dihydrochloride, 2-(carbamoylazo)isobutyronitrile and 4,4'-azobis(4-cyanovaleric acid). The compounds mentioned are used in normal quantities, preferably within a range from about 0.01 to about 5, preferably from about 0.1 to about 2 mol %, respectively based on the quantity of the monomers to be polymerized.

The redox catalysts have as oxidic components at least one of the above-indicated per-compounds and as reducing components preferably ascorbic acid, glucose, sorbose, mannose, ammonium or alkali metal hydrogensulfite, -sulfate, -thiosulfate, -hyposulfite or -sulfide, metal salts, such as iron(II) ions or silver ions or sodium hydroxymethylsulfoxylate. Preferably used as reducing components of the redox catalysts are ascorbic acid or sodium pyrosulfite. Based on the quantity of monomers to be used in the polymerization, about $1 \times 10^{-5}$ to about 1 mol % of the reducing component of the redox catalyst and about $1 \times 10^{-5}$ to about 5 mol % of the oxidising component of the redox catalyst are used. In place of the oxidising components of the redox catalyst, or in addition thereto, one or more preferably water soluble azo compounds can be used.

If the polymerization is initiated by action of energetic beams, so-called photo-initiators are generally used. These can comprise for example so-called $\alpha$-splitters, H-abstracting systems or also azides. Examples of such initiators are benzophenone derivatives such as Michler's ketone, phenanthrene derivatives, fluorine derivatives, anthraquinone derivatives, thioxanthone derivatives, cumarin derivatives, benzoinether and derivatives thereof, azo compounds such as the above-mentioned radical formers, substituted hexaarylbisimidazoles or acylphosphine oxides. Examples of azides are: 2-(N,N-dimethylamino)ethyl-4-azidocinnamate, 2-(N,N-dimethylamino)ethyl-4-azidonaphthylketone, 2-(N,N-dimethylamino)ethyl-4-azidobenzoate, 5-azido-1-naphthyl-2'-(N,N-dimethylamino)ethylsulfone, N-(4-sulfonylazidophenyl)maleinimide, N-acetyl-4-sulfonylazidoaniline, 4-sulfonylazidoaniline, 4-azidoaniline, 4-azidophenacyl bromide, p-azidobenzoic acid, 2,6-bis(p-azidobenzylidene)cyclohexanone and 2,6-bis(p-azidobenzylidene)-4-methylcyclohexanone. The photo-initiators, when used, are generally employed in quantities from about 0.01 to about 5 wt. % based on the monomers to be polymerized.

A redox system used preferentially according to the invention comprises hydrogen peroxide, sodium peroxodisulfate and ascorbic acid. Generally azo compounds are preferred as initiators according to the invention, wherein azo-bis(amidinopropane) dihydrochloride is particularly preferred.

As a rule the polymerization is initiated with the initiators in a temperature range of about 30 to about 90° C.

The polymer gel is dried to achieve a water content of about 0.5 to about 25 wt. %, preferably of about 1 to about 10 wt. %, at temperatures which generally lie in the region of about 100 to about 200° C.

In a preferred embodiment the absorbent polymer structure (Pu1) or (Pu2) used in the process according to the invention has at least one of the following properties (ERT=EDANA Recommended Test):

(A) the maximum absorption of about 0.9 wt. % NaCl solution according to ERT 440.1-99 is within a range from at least about 10 to about 1000, preferably from about 15 to about 500 and particularly preferably from about 20 to about 300 g/g, (B) the part extractable with 0.9 wt. % NaCl solution according to ERT 470.1-99 amounts to less than about 30, preferably less than about 20 and particularly preferably less than about 10 wt. %, based on the absorbent polymer structure (Pu1) or (Pu2), (C) The bulk density according to ERT 460.1-99 is within a range from about 300 to about 1000, preferably about 310 to about 800 and particularly preferably about 320 to about 700 g/l, (D) The pH value according to ERT 400.1-99 for 1 g of the absorbent polymer structure (Pu1) or (Pu2) in 1 l water is within a range from about 4 to about 10, preferably about 5 to about 9 and particularly preferably about 5.5 to about 7.5.

(E) The CRC value according to ERT 441.1-99 is within a range from about 10 to about 100, preferably about 15 to about 80 and particularly preferably about 20 to about 60 g/g.

The property combinations of two or more properties arising from the above properties produce respectively preferred embodiments of the process according to the invention. Further particularly preferred embodiments are processes, in which the absorbent polymer structure (Pu1) or (Pu2) has the following properties or combinations of properties depicted as alphabetic characters or combinations of alphabetic characters: A, B, C, D, E, AB, AC, AD, AE, ABC, ABD, ABE, ACD, ACE, ADE, ABCD, ABCE, ABDE, ACDE, ABCDE.

The bringing into contact of the absorbent polymer structure (Pu1) or (Pu2) with the aqueous solution occurs in processes according to the invention preferably by good mixing of the aqueous solution with the absorbent polymer structure (Pu1) or (Pu2). The aqueous solution is preferably essentially free from organic solvents, in particular free from polyvalent alcohols and polyalkyleneglycol ethers, particularly preferably free from diethyleneglycolmonomethylether and 1,3-butanediol. In this context it is particularly preferred, that by an aqueous solution is understood a solution, which is based on water to at least about 50 wt. %, particularly preferred to at least about 60 wt. %, further preferred to at least about 70 wt. % and even more preferred to at least about 90 wt. %, respectively based on the total quantities of all components present in the aqueous solution which are liquid at room temperature.

Thereby the chemical cross-linker can be present from the outset in the aqueous solution containing the inorganic compound in dispersed colloidal form. It is however also possible that the chemical cross-linker and the dispersed colloidal inorganic compound be brought into contact separately, but preferably simultaneously, with the absorbent polymer structure (Pu1) or (Pu2). In this case preferably two separate solutions, of which the one comprises the chemical cross-linker and the other the inorganic compound in dispersed colloidal form, are mixed preferably simultaneously with the absorbent polymer structure (Pu1) or (Pu2), whereby however a homogeneous distribution of the chemical cross-linker and of the inorganic compound in dispersed colloidal form must be ensured.

Suitable mixing aggregates for the application of the components are e.g. the Patterson-Kelley mixer, DRAIS turbulence mixer, Lödige mixer, Ruberg mixer, screw mixer, pan mixer and fluidised bed mixer as well as continually functioning vertical mixers, in which the polymer structure is mixed with a fast frequency by means of rotating knives (Schugi mixer). The absorbent polymer structure (Pu1) or (Pu2) in the process according to the invention is brought into contact with at most about 20 wt. %, particularly preferably with at most about 15 wt. %, more preferably with at most about 10 wt. %, even more preferably with at most about 5 wt. % water and most preferably with less than about 3 wt. %, respectively based on the weight of the absorbent polymer structure (Pu1) or (Pu2).

In a use of absorbent polymer structures (Pu1) or (Pu2) in the form of preferably ball-shaped particles it is, according to the invention, further preferred that the bringing into contact occurs in such a way that merely the outer portion, but not the inner portion, of the particle-shaped absorbent polymer structure, is brought into contact with the inorganic compound in dispersed colloidal form. In this context, as outer portion of the polymer structure is preferably understood that portion, which is characterized in that the distance of each spatial point lying in this portion from the centre of the particle amounts to at least about 50%, particularly preferred at least about 75%, further preferred at least about 90% and even more preferred at least about 95% of the radius of the particle-shaped absorbent polymer structure. The thus achieved inhomogeneous immobilization of the dispersed colloidal inorganic compound on the polymer structure is, according to the invention, achieved by bringing the dry polymer structure into contact with the aqueous solution and moreover using only such small quantities of water that the absorption of the aqueous liquid is only achieved in the outer portion of the absorbent polymer structure.

It is further preferred in processes according to the invention that at least about 30 wt. %, particularly preferred at least about 60 wt. % and above all preferred at least about 90 wt. % of the dispersed colloidal inorganic compound has a particle size within a range from about 1 to about 100, preferably from about 5 to about 80 and above all preferably from about 6 to about 50 nm.

The inorganic compound is, according to the process according to the invention, brought into contact with the absorbent polymer structure (Pu1) or (Pu2) preferably in a quantity from about 0.001 to about 10 wt. %, particularly preferably from about 0.01 to about 5 wt. % and above all preferably from about 0.05 to about 1.5 wt. % based on the absorbent polymer structure (Pu1) or (Pu2).

As inorganic compound can be used all water insoluble inorganic compounds from which stable, dispersed colloidal, preferably single-phase aqueous solutions can be obtained, which at about 20° C. and normal pressure, over a time period of at least about 6 h, preferably at least about 24 h and particularly preferably at least about 72 h to about 6 months, show no phase separation, such as for example the deposition of a solid inorganic precipitate.

By a dispersed colloidal solution is preferably understood a solution which contains particles with a particle diameter within a range from about 100 to about 1000 Å ($10^{-4}$ to $10^{-5}$ cm). These solutions have the property of scattering in all directions a light beam passed through the solution, so that the course of the light beam through the solution can be traced (Tyndall effect, see Hollemann-Wiberg, *Lehrbuch der anorganischen Chemie*, 91st-100th edition, de Gruyter-Verlag, page 765).

As particularly preferred dispersed colloidal inorganic compound used in processes according to the invention are particles comprising polysilicic acid. A dispersed colloidal solution containing such particles (silica sol) can for example be obtained by careful acidification of sodium silicate solutions reacting as base as a result of hydrolysis, or by dissolving molecular silicic acid in water and possibly subsequently stabilising the resulting dispersed colloidal solution. The exact production of such silica sols is known to the person skilled in the art and is for example described in Jander Blasius, *Lehrbuch der analytischen und präparativen anorganischen Chemie*, S. Hirzel Verlag, Stuttgart.

Besides the dispersed colloidal silicic acid, according to the invention, iron(III) oxide hydrate sols, tin(IV) oxide hydrate sols or sols based on silver halides, in particular silver chloride, are further particularly preferred as dispersed colloidal inorganic compound.

By chemical cross-linkers, which in processes according to the invention are contained in the aqueous solution, are understood preferably compounds which have at least two functional groups, which groups can react with functional groups of a polymer in a condensation reaction (=condensation cross-linker), in an addition reaction or in a ring-opening reaction, or polyvalent metal cations which enable cross-linking of the polymer by means of electrostatic interactions between the polyvalent metal cation and the functional groups of a polymer. As chemical cross-linker for secondary cross-linking of the outer portion of the absorbent polymer structure (Pu1) or (Pu2)—also named "secondary cross-linker"—in processes according to the invention are preferred those that were mentioned in the context of the cross-linkers (α3) as cross-linkers of cross-linker classes II and IV.

Among these compounds condensation cross-linkers are particularly preferred as secondary cross-linkers such as for example diethyleneglycol, triethyleneglycol, polyethyleneglycol, glycerine, polyglycerine, propyleneglycol, diethanolamine, triethanolamine, polyoxypropylene, oxyethylene-oxypropylene block copolymers, sorbitan fatty acid esters, polyoxyethylenesorbitan fatty acid esters, trimethylolpropane, pentaerythritol, polyvinylalcohol, sorbitol, 1,3-dioxolan-2-one (ethylenecarbonate), 4-methyl-1,3-dioxolan-2-one (propylenecarbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, 1,3-dioxolan-2-one, poly-1,3-dioxolan-2-one.

Particularly preferred for use as secondary cross-linker is ethylene carbonate.

The secondary cross-linker in processes according to the invention is used preferably in a quantity within the range from about 0.01 to about 30, particularly preferably about 0.1 to about 20 and above all preferably from about 0.3 to about 5 wt. %, based on the absorbent polymer structure (Pu1) or (Pu2).

After the chemical cross-linker and the aqueous solution containing the inorganic compound have been brought into contact with the absorbent polymer structure (Pu1) or (Pu2), the secondary cross-linking reaction occurs in processes according to the invention by heating the absorbent polymer structure at temperatures within the range from about 40 to about 300° C., preferably from about 80 to about 250° C. and particularly preferably from about 150 to about 220° C. The optimal time duration of the secondary heating can be easily investigated for the individual cross-linker types and dispersed colloidal inorganic compounds. The secondary heating time limit is thus reached when the desired property profile of the superabsorber is destroyed as a result of heat damage. The thermal treatment can be carried out in typical dryers or ovens, examples being cylindrical rotary oven, fluidised bed oven, disk drier, paddle drier or infrared drier.

It is preferred according to the invention that as a result of the thermal treatment the outer portion of the absorbent polymer structure is more strongly cross-linked than the inner portion and that by the thermal treatment the inorganic compound is at least partly immobilized in the outer portion. It is moreover preferred in this context that the radius of the outer portion be smaller than three times the value of the radius of the inner portion.

In another embodiment of the process according to the invention the outer portion of the absorbent polymer structure before or after, preferably after, being brought into contact with the aqueous solution comprising the chemical cross-linker and the inorganic compound in dispersed colloidal form is brought into contact with a compound comprising $Al^{3+}$ ions. It is therein preferred that the compound comprising $Al^{3+}$ ions, in a quantity within a range from about 0.01 to about 30 wt. %, particularly preferably in a quantity within a range from about 0.1 to about 20 wt. % and above all preferably in a quantity within a range from about 0.3 to about 5 wt. %, respectively based upon the weight of the absorbent polymer structure, be brought into contact with the polymer structure.

The bringing into contact of the outer portion of the absorbent polymer structure with the compound comprising $Al^{3+}$ ions occurs preferably by mixing the absorbent polymer structure (Pa) with the compound under dry conditions or by bringing the absorbent polymer structure (Pa) into contact with a fluid comprising a solvent, preferably water, water-miscible organic solvents such as for example methanol or ethanol or mixtures of at least two therefrom and the compound comprising $Al^{3+}$ ions, wherein the bringing into contact occurs preferably by spraying the polymer particles with the fluid and mixing. In this context it is moreover preferred that the bringing into contact of the absorbent polymer structure (Pa) with the fluid comprising the compound comprising $Al^{3+}$ ions occurs in a two-step process. Therein the two-step process comprises a first mixing process, in which a plurality of absorbent polymer structures are mixed with the fluid, and a second mixing process, in which the fluid is homogenised in the interior of the polymer particles, wherein the polymer particles in the first mixing process are mixed with a speed such that the movement energy of the individual polymer particles in the medium is larger than the adhesion energy between the individual polymer particles and the polymer particles in the second mixing process are mixed thoroughly with a lower speed than in the first mixing process.

Absorbent polymer structures with improved absorption properties can be obtained by the treatment of the absorbent polymer structure (Pa) with the fluid comprising the compound comprising $Al^{3+}$ ions by the above described two-step process.

The compound comprising $Al^{3+}$ ions is preferably thereby included in the fluid without consideration of water of crystallisation in a quantity within a range from about 0.1 to about 50 wt. %, particularly preferably in a quantity within a range from about 1 to about 30 wt. %, respectively based on the total weight of the fluid. It is further preferred that the fluid is brought into contact with the absorbent polymer structure (Pa), in a quantity within a range from about 0.01 to about 15 wt. %, particularly preferably in a quantity within a range from about 0.05 to about 6 wt. %, respectively based on the weight of the absorbent polymer structure (Pa).

Preferred compounds comprising $Al^{3+}$ ions are $AlCl_3 \times 6 H_2O$, $NaAl(SO_4)_2 \times 12 H_2O$, $KAl(SO_4)_2 \times 12 H_2O$ or $Al_2(SO_4)_3 \times 14\text{-}18 H_2O$.

The above invention concerns furthermore absorbent polymer structures (Pa) which are obtainable by the above-described processes according to the invention.

In addition the invention concerns an absorbent polymer structure (Pa) comprising an inner portion as well as an outer portion surrounding the inner portion, wherein the outer portion is more strongly cross-linked than the inner portion, an inorganic compound is at least partly immobilized in the outer portion, preferably only in the outer portion and not in the inner portion, and wherein the absorbent polymer structure (Pa) has at least one of the following properties:

(β1) for a CRC according to ERT 441.1-99<26 g/g a SFC of at least about $80 \cdot 10^{-7}$, preferably of at least about $100 \cdot 10^{-7}$ and particularly preferably of at least about $120 \cdot 10^{-7}$ cm$^3 \cdot$s$\cdot$g$^{-1}$, (β2) for a CRC according to ERT 441.1-99 within the range $\geq 26$ to $<27$ g/g a SFC of at least about $70 \cdot 10^{-7}$, preferably of at least about $90 \cdot 10^{-7}$ and particularly preferably of at least about $110 \cdot 10^{-7}$ cm$^3 \cdot$s$\cdot$g$^{-1}$, (β3) for a CRC according to ERT 441.1-99 within the range $\geq 27$ to $<28$ g/g a SFC of at least about $60 \cdot 10^{-7}$, preferably of at least about $80 \cdot 10^{-7}$ and particularly preferably of at least about $100 \cdot 10^{-7}$ cm$^3 \cdot$s$\cdot$g$^{-1}$, (β4) for a CRC according to ERT 441.1-99 within the range $\geq 28$ to $<29$ g/g a SFC of at least about $45 \cdot 10^{-7}$, preferably of at least about $65 \cdot 10^{-7}$ and particularly preferably of at least about $85 \cdot 10^{-7}$ cm$^3 \cdot$s$\cdot$g$^{-1}$, (β5) for a CRC according to ERT 441.1-99 within the range $\geq 29$ to $<30$ g/g a SFC of at least about $30 \cdot 10^{-7}$, preferably of at least about $50 \cdot 10^{-7}$ and particularly preferably of at least about $70 \cdot 10^{-7}$ cm$^3 \cdot$s$\cdot$g$^{-1}$, (β6) for a CRC according to ERT 441.1-99 within the range $\geq 30$ to $<31$ g/g a SFC of at least about $20 \cdot 10^{-7}$, preferably of at least about $40 \cdot 10^{-7}$ and particularly preferably of at least about $60 \cdot 10^{-7}$ cm$^3 \cdot$s$\cdot$g$^{-1}$, (β7) for a CRC according to ERT 441.1-99 within the range $\geq 31$ g/g a SFC of at least about $10 \cdot 10^{-7}$, preferably of at least about $20 \cdot 10^{-7}$ and particularly preferably of at least about $30 \cdot 10^{-7}$ cm$^3 \cdot$s$\cdot$g$^{-1}$.

The property combinations of two or more properties arising from the above properties produce respectively preferred embodiments of the absorbent polymer structure (Pa) according to the invention. A further particularly preferred embodiment according to the invention is an absorbent polymer structure (Pa), which has the following properties or property combinations depicted as alphabetic characters of combinations of alphabetic characters: β1, β2, β3, β4, β5, β6, β7, wherein β2, β3, β4, β5 and β6 are particularly preferred.

It is further preferred according to the invention that the absorbent polymer structure (Pa) has an Absorbency against Pressure (AAP) according to ERT 442.1-99 under a pressure of 50 g/cm$^2$ of at least about 18 g/g, particularly preferably at least about 20 g/g and above all particularly preferably of at least about 22 g/g.

It is further preferred for the absorbent polymer structure according to the invention that the radius of the outer portion is smaller than double the value of the radius of the inner portion.

In a particularly preferred embodiment of the absorbent polymer structure (Pa), as outer portion of the polymer structure is preferably understood that portion, that is characterized in that the distance of each spatial point lying in this portion from the centre of the particle amounts to at least about 50%, particularly preferably at least about 75%, more preferred at least about 90% and even more preferred at least about 95% of the radius of the particle-shaped absorbent polymer structure.

The inorganic compound which is at least partly immobilized in the outer portion of the absorbent polymer structure (Pa) according to the invention can be any water insoluble inorganic compound from which stable dispersed colloidal aqueous solutions can be obtained.

A particularly preferred inorganic compound which is at least partly immobilized in the outer portion of the absorbent polymer structure (Pa) according to the invention is a condensate of polysilicic acids.

It is further preferred that the above-mentioned characteristics of the absorbent polymer structure (Pa) according to the invention are also valid for the absorbent polymer structure (Pa) obtainable by the processes according to the invention mentioned above.

According to an embodiment according to the invention of the processes according to the invention as well as the absorbent polymer structure (Pa) according to the invention it is preferred that the values of characteristics according to the invention which are given only with a lower limit have an upper limit, which is about 20 times, preferably about 10 times and particularly preferably about 5 times the most preferred value of the lower limit.

The invention further concerns a composite, comprising an above-defined absorbent polymer structure (Pa) and a substrate. The polymer structure (Pa) according to the invention and the substrate are preferably securely bound together. As substrate are preferred films made out of polymers, such as for example out of polyethylene, polypropylene or polyamide, metals, non-woven material, fluff, tissues, fabric, natural or synthetic fibers, or other foams.

Preferred composites according to the invention are sealant materials, cables, absorbent cores as well as diapers and hygiene articles comprising them.

Sealant materials are preferably water-absorbent films, wherein the absorbent polymer structure is worked into a polymer matrix or fiber matrix as substrate. This is carried out preferably by mixing the absorbent polymer structure (Pa) with a polymer or fiber matrix-forming polymer (Pm) and finally binding them, optionally by thermal treatment. In the case where the absorbent structure is used as fibers, yarns can be obtained therefrom which can be spun with additional fibers comprising another material as substrate and then for example bound together by knitting or weaving or be directly bound together, i.e. without being spun with additional fibers. Typical processes herefor are described in H. Savano et al., International Wire & Cable Symposium Proceedings 40, 333 to 338 (1991); M. Fukuma et al., International Wire & Cable Symposium Proceedings, 36, 350 to 355 (1987) and in U.S. Pat. No. 4,703,132.

In the embodiment in which the composite is a cable, the absorbent polymer structure (Pa) as particles can be directly used, preferably beneath the insulation of the cable. In another embodiment of the cable the absorbent polymer structure (Pa) can be used in the form of swellable tension-resistant yarns. According to another embodiment of the cable the absorbent polymer structure (Pa) can be used as swellable film. Furthermore in another embodiment of the cable the absorbent polymer structure can be used as moisture-absorbent cores in the middle of cables. The substrate in the case of the cable forms all components of the cable which contain no absorbent polymer structure (Pa). Hereunder are included conduits, such as electrical lines or light conduits, optical or electrical insulation materials as well as components of the cable which ensure the mechanical applicability of the cable, such as networks, fibers or fabrics made from tension-resistant materials such as synthetic materials and insulators made from rubber or other materials which prevent the destruction of the exterior of the cable.

If the composite is an absorbent core, the absorbent polymer structure (Pa) is worked into a substrate. This substrate can preferably be in the form of fibrous materials. Fibrous materials which can be used in the above invention comprise natural fibers (modified or unmodified) as well as synthetic fibers. Examples of suitable unmodified and modified natural fibers comprise cotton, spanish grass, sugarcane, kemp, flax, silk, wool, cellulose, chemically modified pulp, jute, rayon, ethylcellulose and cellulose acetate. Suitable synthetic fibers can be produced from polyvinylchloride, polyvinylfluoride, polytetrafluoroethylene, polyvinylidenechloride, polyacrylates such as Orion®, Polyvinylacetate, polyethylvinylacetate, soluble or insoluble polyvinylalcohol, polyolefins such as polyethylene (for example PULPEX®) and polypropylenes, polyamides such as nylon, polyesters such as DACRON® or Kodel®, polyurethanes, polystyrenes and the like. The fibers used can comprise only natural fibers, only synthetic fibers or any compatible combination of natural and synthetic fibers.

The fibers used in the above invention can be hydrophilic or hydrophobic, or they can comprise a combination of hydrophilic and hydrophobic fibers. The term "hydrophilic" as used here describes fibers or surfaces of fibers which can be wetted by aqueous liquids (for example aqueous bodily liquids) which are deposited on these fibers. Hydrophilicity and wettability are typically defined in terms of the contact angle and the surface tension of the concerned liquids and solids. This is discussed in detail in a publication of the American Chemical Society with the title "Contact Angle, Wettability and Adhesion", published by Robert F. Gould (copyright 1964). A fiber or the surface of a fiber is wetted by a liquid (i.e. it is hydrophilic) if either the contact angle between the liquid and the fiber or the surface thereof amounts to less than about 90°, or if the liquid tends to distribute itself spontaneously over the surface, wherein both conditions are normally simultaneous. On the other hand a fiber or the surface of a fiber is considered as hydrophobic, if the contact angle is larger than about 90° and the liquid does not spread spontaneously on the surface of the fibre.

Preferred fibers according to the invention are hydrophilic fibers. Suitable hydrophilic fibers comprise cellulose fibers, modified cellulose fibers, rayon, polyester fibers, such as polyethyleneterephthalate (for example DACRON®), hydrophilic nylon (HYDROFIL®) and the like. Suitable hydrophilic fibers can also be obtained by hydrophilising hydrophobic fibers, such as thermoplastic fibers, which are based for example on polyolefins such as polyethylene or polypropylene or on polyacrylates, polyamides, polystyrenes, polyurethanes and the like, treated with a surface-active agent or treated with silica. For reasons of availability and of cost cellulose fibers, in particular pulp fibers, are preferred for use in the above invention. Further preferred hydrophilic fibers for use in the above invention are chemically stiffened cellulose fibers. The term "chemically stiffened cellulose fibers" describes therein cellulose fibers which are stiffened by means of a chemical medium in order to increase the stiffness of the fibers under dry as well as under aqueous conditions. Such media can be chemical stiffening agents, which for example cover and/or impregnate the fibers. They can however also be chemical stiffening agents which effect a stiffening by changing the chemical structure of the fibers, for example brought about by cross-linking of polymer chains. Polymer-stiffening agents which can cover or impregnate the cellulose fibers comprise: cationic starches which have nitrogen-containing groups (for example amino groups), which are obtainable from the National Starch and Chemical Corp., Bridgewater, N.J., USA, latexes, moisture-resistant resins such as polyamide epichlorohydrin resin (for example Kymene® 557H, Hercules, Inc., Wilmington, Del., USA), polyacrylamide resins, as described for example in U.S. Pat. No. 3,556,932, commercially available polyacrylamides such as Parez® 631 NZ of the American Cyanamid Co., Stanfort, Conn., USA, ureaformaldehydes as well as melamineformaldehyde resins. Fibers which were stiffened by cross-linking connections in individual forms (i.e. the individually stiffened fibers as well as the process for their production) are for example described in U.S. Pat. No. 3,224,926, U.S. Pat. No. 3,440,135, U.S. Pat. No. 3,932,209 as well as in U.S. Pat. No. 4,035,147. Preferred cross-linking agents are glutaraldehyde, glyoxal, formaldehyde, glyoxalic acid, oxydisuccinic acid and citric acid. The stiffened cellulose fibers obtained by cross-linking or coating, impregnation or cross-linking can be twisted or curled, the fibers are preferably twisted and additionally curled.

Besides the above-mentioned fibrous materials the core can also comprise thermoplastic materials. On melting, at least a part of this thermoplastic material, typically because of the capillary gradient, penetrates between the fibers to the intersections of the fibers. These intersections become binding positions for the thermoplastic material. If the element is cooled, the thermoplastic material solidifies at these intersections, to form binding positions which hold together the matrix or the tissue of fibers in each of the respective layers. The thermoplastic materials can be in various forms, such as particles, fibers or combinations of particles and fibers. These materials can comprise a plurality of thermoplastic polymers, selected from polyolefins, such as polyethylene (for example PULPEX®) and polypropylene, polyesters, co-polyesters, polyvinylacetates, polyethylvinylacetates, polyvinylchlorides, polyvinylidenechlorides, polyacrylates, polyamides, co-polyamides, polystyrenes, polyurethanes and copolymers of the above materials, such as vinylchloride/vinylacetate and the like. For cores, predominantly materials made from cellulose, preferably fibrous, can be used as substrate.

In a further embodiment of the core this core comprises besides the substrate and the absorbent polymer structure (Pa) further substances in the form of powders, such as for example odour binding substances such as cyclodextrins, zeolites, inorganic or organic salts or similar materials.

In one embodiment of the absorbent core the absorbent polymer structure (Pa) is worked in a quantity within the range from about 10 to about 90, preferably from about 20 to about 80 and particularly preferably from about 40 to about 70 wt. %, based on the core. In one embodiment of the core the absorbent polymer structure (Pa) is worked into the core as particles. In this way the absorbent polymer structures (Pa) can be homogeneously distributed in the fibrous material, they can be positioned in layered fashion between the fibrous material or the concentration of the absorbent polymer structure (Pa) can have a gradient within the fibrous material. In another embodiment of the core the absorbent polymer structure (Pa) is worked into the core as fibers.

Several different absorbent polymer particles, which differ for example in the rate of absorption, in the permeability, in the retention capacity, in the absorption against pressure, the grain distribution or also in the chemical composition, can optionally be employed simultaneously. These various polymer particles can be put already mixed together into the absorbent pad or positioned in the core with local differentiations. Such a differential positioning can occur in the direction of the thickness of the core or of the length or breadth of the core.

The core can be combined by conventional processes known to one skilled in the art, such as those known to one skilled in the art generally among drum-forming, by means of forming wheels, -pockets and product forms and appropriately adapted dosing arrangements. Besides this there are modern, established process such as the so-called airlaid processes (e.g. EP 850 615, U.S. Pat. No. 4,640,810) with all forms of the dosing, depositing of the fibers and consolidation such as hydrogen bonding (e.g. DE 197 50 890), thermobonding, latex bonding, (e.g. EP 850 615) and hybrid bonding, the so-called wetlaid processes (e.g. WO 99/49905), carding processes, meltblown processes, spunblown processes as well as similar processes for producing superabsorbent non-wovens (in the sense of the definition of the EDANA, Brussels) also in combinations of these processes with and among usual methods for producing the cores. Further processes which could be used are the production of laminates in the broadest sense as well as of extruded and co-extruded, wet- and dry- as well as additionally reinforced structures.

In a further embodiment of the absorbent core this core comprises besides the substrate and the absorbent polymer structure (Pa) worked into the substrate, which serve as storage layer for the bodily liquids, an absorbent layer which preferably serves to absorb and distribute quickly the liquid in the core. Thus the absorption layer can be arranged directly over the storage layer, it being however also possible that the absorption layer is separated from the storage layer by a preferably liquid-stable interface. This interface serves then in the first instance as support substrate for the absorption layer and the storage layer. Preferred materials for this interface are polyester spun fleeces or fleeces made from polypropylene, polyethylene or nylon.

In one embodiment of the core according to the invention the absorbent layer is free from absorbent polymer. The absorbent layer can have any suitable size and must not exceed the total length or breadth of the storage layer. The absorbent layer can for example be in the form of a strip or a patch. The total absorbent layer is preferably hydrophilic but can also have hydrophobic components. The absorbent layer can comprise a woven material, a fleece material, or another suitable type of material. The absorbent layer is preferably based on hydrophobic polyethylene-terephthalate fibers (PET fibers), chemically stiffened cellulose fibers or on mixtures of these fibers. Further suitable materials are polypropylene, polyethylene, nylon or biological fibers. If the absorbent layer comprises a fleece material, said layer can be produced by a plurality of different processes. These comprise wet-laying, application in an air stream, application in a melt, forming as spun fleece, carding, (this comprises thermal joining, joining with solvents or joining with the melt-spin process). The last mentioned processes (forming as spun fleece and carding) are preferred when it is desirable to align the fibers in the absorbent layer, since it is easier in such processes to align the fibers in a single direction. A particularly preferred material for the absorbent layer is a PET-spun fleece.

In the embodiment in which the composite is a diaper, the components of the diaper which are different to the absorbent polymer structure comprise the substrate of the composite. In a preferred embodiment the diaper comprises an above-described core. In this case the components of the diaper which are different to the core comprise the substrate of the composite. In general a composite used as a diaper comprises a water-impermeable lower layer, a water-permeable, preferably hydrophobic, upper layer and a layer comprising the absorbent polymer structure (Pa), which is arranged between the lower layer and the upper layer. This absorbent polymer-comprising layer is preferably a heretofore-described core. The lower layer can comprise all materials known to one skilled in the art, wherein polyethylene or polypropylene are preferred. The upper layer can likewise comprise all suitable material known to one skilled in the art, wherein polyesters, polyolefins, viscose and the like are preferred, which give a sufficiently porous layer to ensure a satisfactory liquid permeability of the upper layer. In this context reference is made to the disclosure in U.S. Pat. No. 5,061,295, U.S. Pat. No. Re. 26,151, U.S. Pat. No. 3,592,194, U.S. Pat. No. 3,489,148 as well as U.S. Pat. No. 3,860,003.

The invention further comprises a process for producing a composite, wherein an absorbent polymer structure according to the invention and a substrate and optionally a suitable additive are brought into contact with each other. The bringing into contact occurs preferably by wetlaid and airlaid processes, compression, extrusion and mixing.

In addition the invention comprises a composite which is obtainable by the above processes.

The invention further comprises chemical products, in particular foams, formed bodies, fibers, sheets, films, cables, sealant materials, liquid-absorbing hygiene articles, carriers for plant or mushroom growth regulating media or plant protection agents, additives for building materials, packing materials or soil additives, which comprise the absorbent polymer structure (Pa) according to the invention or the above-described substrate.

The invention additionally comprises the use of absorbent polymer structures (Pa) according to the invention or of the above described substrate in chemical products, in particular in foams, formed bodies, fibers, sheets, films, cables, sealant materials, liquid-absorbing hygiene articles, carriers for plant or mushroom growth-regulating media or plant protection agents, additives for building materials, packing materials or soil additives.

In the use as carriers for plant or mushroom growth-regulating media or plant protection agents, it is preferred that the plant or mushroom growth-regulating media or plant protection agents can be released over a time period controlled by the carrier.

The invention further comprises an aqueous solution comprising at least one chemical cross-linker and at least one inorganic compound in dispersed colloidal form, wherein the chemical cross-linker and the inorganic compound correspond to those chemical cross-linkers or inorganic compounds which have already been mentioned in the context of the previously described processes according to the invention for producing absorbent polymer structures (Pa).

The chemical cross-linker is present in the aqueous solution according to the invention preferably in a quantity from about 5 to about 70 wt. %, particularly preferably from about 20 to about 60 wt. % and above all preferably from about 30 to about 50 wt. %, based on the quantity of water in the aqueous solution.

The inorganic compound is present in the aqueous solution according to the invention preferably in a quantity from about 1 to about 40 wt. %, particularly preferably from about 1.5 to about 35 wt. % and above all preferably from about 2.5 to about 32 wt. %, based on the quantity of water in the aqueous solution.

The above invention is also related to a process for producing this aqueous solution, wherein an aqueous solution comprising at least one inorganic compound in dispersed colloidal form is mixed with at least one chemical cross-linker. In this process according to the invention the chemical cross-linker can be mixed as is or in the form of an aqueous solution with the aqueous solution comprising the inorganic compound in dispersed colloidal form.

The invention is also related to an aqueous solution which is obtainable by the above process.

The invention is further related to the use of an aqueous solution comprising at least one chemical cross-linker and at least one inorganic compound in dispersed colloidal form or the use of an aqueous solution which is obtainable by the above process for producing an aqueous solution, for treating the outer portion of an absorbent polymer structure (Pu1) or (Pu2). The treatment occurs therein in the manner and way already set out previously in the context of the process according to the invention for treating the outer portion of an absorbent polymer structure (Pu1) or (Pu2). The absorbent polymer structure (Pu1) or (Pu2) comprises that absorbent polymer structure (Pu1) or (Pu2) which has also already been described in the context of the process according to the invention for treating the outer portion of an absorbent polymer structure (Pu1) or (Pu2).

The invention finally comprises the use of an aqueous solution comprising at least one chemical cross-linker and at least one inorganic compound in dispersed colloidal form or the use of an aqueous solution obtainable according to the above process for producing an aqueous solution for the tuning of at least one of the following properties in an absorbent polymer structure (Pu1) or (Pu2):

(γ1) Saline Flow Conductivity (SFC),
(γ2) Centrifugation Retention Capacity (CRC) or
(γ3) Absorbency against Pressure (AAP).

The property combinations resulting from the above properties, of combinations of two or more of these properties produce respectively preferred forms of the use according to the invention of the aqueous solution according to the invention. As further embodiments according to the invention, particularly preferred is a use of the aqueous solution for the tuning of the following properties or property combinations: γ1, γ2, γ3, γ1γ2, γ1γ3, γ2γ3, γ1γ2γ3.

The invention is more closely illustrated by, but not limited to, examples.

EXAMPLES

Production of the Untreated Absorbent Polymer Structure (PU1) or (PU2)

Powder A

A monomer solution comprising 280 g acrylic acid, which has been neutralized to 70 mol % with sodium hydroxide, 466.8 g water, 1.4 g polyethyleneglycol-300-diacrylate and 1.68 g allyloxypolyethyleneglycol acrylic acid ester is deoxygenated by flushing with nitrogen and cooled to the start temperature of 4° C. After reaching the start temperature the initiator solution (0.1 g 2,2'-azobis-2-amidinpropane dihydrochloride in 10 g $H_2O$, 0.3 g sodium peroxydisulfate in 10 g $H_2O$, 0.07 g 30% hydrogen peroxide solution in 1 g $H_2O$ and 0.015 g ascorbic acid in 2 g $H_2O$) was added. After the end temperature of ca. 100° C. is reached, the resulting gel was reduced to small pieces and dried at 150° C. for 90 minutes. The dried polymerizatepolymerizate was coarsely ground, finely ground and sieved to a powder with a particle size of 150 to 850 μm.

Powder A has a retention capacity of 28.8 g/g.

Powder B

A monomer solution comprising 280 g acrylic acid, which has been neutralized to 70 mol % with sodium hydroxide, 467.6 g water, 0.98 g polyethyleneglycol-300-diacrylate and 1.26 g allyloxypolyethyleneglycol acrylic acid ester is deoxygenated by flushing with nitrogen and cooled to the start temperature of 4° C. After reaching the start temperature the initiator solution (0.1 g 2,2'-azobis-2-amidinpropane dihydrochloride in 10 g $H_2O$, 0.3 g sodium peroxydisulfate in 10 g $H_2O$, 0.07 g 30% hydrogen peroxide solution in 1 g $H_2O$ and 0.015 g ascorbic acid in 2 g $H_2O$) was added. After the end temperature of ca. 100° C. was reached, the resulting gel was broken up and dried at 150° C. for 90 minutes. The dried polymerizate was coarsely ground, finely ground and sieved to a powder with a particle size of 150 to 850 μm.

Powder B has a retention capacity of 31.2 g/g.

Powder C

A monomer solution comprising 280 g acrylic acid, which has been neutralized to 70 mol % with sodium hydroxide, 468.6 g water, 0.42 g polyethyleneglycol-300-diacrylate and 0.84 g allyloxypolyethyleneglycol acrylic acid ester is deoxygenated by flushing with nitrogen and cooled to the start temperature of 4° C. After reaching the start temperature the initiator solution (0.1 g 2,2'-azobis-2-amidinpropane dihydrochloride in 10 g $H_2O$, 0.3 g sodium peroxydisulfate in 10 g $H_2O$, 0.07 g 30% hydrogen peroxide solution in 1 g $H_2O$ and 0.015 g ascorbic acid in 2 g $H_2O$) was added. After the end temperature of ca. 100° C. was reached, the resulting gel was broken up and dried at 150° C. for 90 minutes. The dried polymerizate was coarsely ground, finely ground and sieved to a powder with a particle size of 150 to 850 μm.

Powder C has a retention capacity of 37.1 g/g.

The quantities given in the following examples, in which the individual components, such as for example the cross-linker, the water or the silicic acid sol, are used for treatment of the outer portion of the untreated absorbent polymer structure (Pu1) or (Pu2), should be understood to be quantities based on the weight of the untreated absorbent polymer structure (Pu1) or (Pu2).

Influence of the Treatment of the Outer Portion of the Untreated Absorbent Polymer Structure (PU1) on the Retention; the Permeability and the Absorption Under Pressure

Example 1

50 g powder A is mixed with vigorous stirring by means of a Krups cake mixer with a solution of 0.5 g ethylene carbonate, 0.42 g silicic acid sol (product Levasil® 200 from Bayer AG, solid components ca. 30 wt. %) and 1.08 g water and finally heated for 30 min. in an oven set at 180° C.

Example 2

50 g powder A is mixed with vigorous stirring by means of a Krups cake mixer with a solution of 0.5 g ethylene carbonate, 0.84 g silicic acid sol (product Levasil® 200 from Bayer AG, solid components ca. 30 wt. %) and 0.66 g water and finally heated for 30 min. in an oven set at 180° C.

Example 3

50 g powder B is mixed with vigorous stirring by means of a Krups cake mixer with a solution of 0.5 g ethylene carbonate, 0.42 g silicic acid sol (product Levasil® 200 from Bayer AG, solid components ca. 30 wt. %) and 1.08 g water and finally heated for 30 min. in an oven set at 180° C.

Example 4

50 g powder B is mixed with vigorous stirring by means of a Krups cake mixer with a solution of 0.5 g ethylene carbonate, 0.84 g silicic acid sol (product Levasil® 200 from Bayer AG, solid components ca. 30 wt. %) and 0.66 g water and finally heated for 30 min. in an oven set at 180° C.

Example 5

50 g powder C is mixed with vigorous stirring by means of a Krups cake mixer with a solution of 0.5 g ethylene carbonate, 0.42 g silicic acid sol (product Levasil® 200 from Bayer AG, solid components ca. 30 wt. %) and 1.08 g water and finally heated for 30 min. in an oven set at 180° C.

Comparison Example 1

50 g powder A is mixed with vigorous stirring by means of a Krups cake mixer with a solution of 0.5 g ethylene carbonate and 1.5 g water and finally heated for 30 min. in an oven set at 180° C.

Comparison Example 2

50 g powder B is mixed with vigorous stirring by means of a Krups cake mixer with a solution of 0.5 g ethylene carbonate and 1.5 g water and finally heated for 30 min. in an oven set at 180° C.

Comparison Example 3

The cross-linked polymer structure obtained from Comparison Example 2 is mixed with vigorous stirring with 0.84 g silicic acid sol (product Levasil® 200 from Bayer AG, solid components ca. 30 wt. %) and 0.16 g water. The product does not undergo any final tempering step.

Comparison Example 4

The cross-linked polymer structure obtained from Comparison Example 2 is mixed with vigorous stirring with 0.84 g silicic acid sol (product Levasil® 200 from Bayer AG, solid components ca. 30 wt. %) and 0.16 g water and finally heated for 60 min. in an oven set at 100° C.

Comparison Example 5

50 g powder B is mixed with vigorous stirring by means of a Krups cake mixer with a solution of 0.5 g ethylene carbonate, 0.125 g Aerosil® (pyrogenic silicic acid sol from Degussa AG) and 2 g water and finally heated for 30 min. in an oven set at 180° C. Increased quantities of water were necessary to produce the suspension of Aerosil® in water. It is nonetheless not possible to obtain an easily dosable suspension, since the Aerosil® used deposits very quickly and a homogeneous dosage into powder B is not possible. The coated polymer tends to form clumps and is inhomogeneous.

Comparison Example 6

50 g powder C is mixed with vigorous stirring by means of a Krups cake mixer with a solution of 0.5 g ethylene carbonate and 1.5 g water and finally heated for 30 min. in an oven set at 180° C.

Comparison Example 7

50 g powder B is mixed with vigorous stirring by means of a Krups cake mixer with a solution of 0.25 g diethylene glycol monomethyl ether, 0.25 g silicic acid sol (product Levasil® 200 from Bayer AG, solid components ca. 30 wt. %) and 1.25 g water and finally heated for 3 min. in an oven set at 120° C. This treatment corresponds to the treatment according to example 1 in JP 1994/16822.

Comparison Example 8

50 g powder B is mixed with vigorous stirring by means of a Krups cake mixer with a solution of 0.25 g 1,3-butandiol, 0.25 g silicic acid sol (product Levasil® 200 from Bayer AG, solid components ca. 30 wt. %) and 1.25 g water and finally heated for 3 min. in an oven set at 120° C. This treatment corresponds to the treatment according to example 2 in JP 1994/16822.

The properties of the absorbent structures obtained in examples 1 to 4 as well as in the comparison examples 1 to 8 are summarised in the following Table 1.

The absorbent polymer structures produced according to the invention show a significant improvement in permeability (SFC) with retention remaining the same or even increasing compared with products in which the outer portion was cross-linked in the absence of a silicic acid sol (examples 1 to 4, comparison examples 1 and 2). A secondary treatment of the already cross-linked polymer structure, with silicic acid, does not lead to the desired result (comparison example 3, 4 and 6) irrespective of the subsequent thermal treatment.

The addition of Aerosil® 200 during the secondary cross-linking does not lead to comparably good superabsorber characteristics (comparison example 5). Furthermore, increased quantities of Aerosil® can no longer be dispersed in an acceptable quantity of water and are thereby no longer dispersible.

Comparison example 7 and 8 show that in the examples according to the invention of the unexamined JP 1994/16822 it is not possible to achieve a good performance of the polymer with respect to its permeability and retention.

TABLE 1

| | SFC ($10^{-7} \cdot cm^3 \cdot s \cdot g^{-1}$) | AAP at 50 g/cm$^2$ (g/g) | CRC (g/g) |
|---|---|---|---|
| Example 1 | 140 | 23.5 | 27 |
| Example 2 | 150 | 23.5 | 27.2 |
| Example 3 | 100 | 24 | 29 |
| Example 4 | 110 | 24 | 29 |
| Comparison Example 1 (without silicic acid sol) | 50 | 24.5 | 26.4 |
| Comparison Example 2 (without silicic acid sol) | 30 | 25 | 27.8 |
| Comparison Example 3 (after secondary cross-linking with silicic acid sol) | 25 | 24 | 28.1 |
| Comparison Example 4 (after secondary cross-linking with silicic acid sol and heating) | 30 | 24 | 28.7 |
| Comparison Example 5 (pyrogenic silicic acid) | 55 | 23 | 29 |
| Comparison Example 6 (without silicic acid sol) | 17 | 25 | 31.6 |
| Comparison Example 7 (JP 1994/16822) | 0 | 9 | 31.3 |
| Comparison Example 8 (JP 1994/16822) | 0 | 9 | 31.2 |

Influence of the Treatment of the Outer Portion of the Untreated Absorbent Polymer Structure (PU1) on the Agglomeration Tendency of the Polymer Structure Example 6

50 g powder B is mixed with vigorous stirring by means of a Krups cake mixer with a solution of 0.5 g ethylene carbonate, 0.125 g silicic acid sol (product Levasil® 200 from Bayer AG, solid components ca. 30 wt. %) and 1.38 g water. Finally a pressed part is prepared from the absorbent polymer structure which has been brought into contact with the aqueous solution and the density thereof and the pressure necessary to destroy the pressed part determined.

Example 7

50 g powder B is mixed with vigorous stirring by means of a Krups cake mixer with a solution of 0.5 g ethylene carbonate, 0.125 g silicic acid sol (product Levasil® 200 from Bayer AG, solid components ca. 30 wt. %) and 1.25 g water. Finally a pressed part is prepared from the absorbent polymer structure which has been brought into contact with the aqueous solution and the density thereof and the pressure exerted to destroy the pressed part determined.

Comparison Example 9

50 g powder B is mixed with vigorous stirring by means of a Krups cake mixer with a solution of 0.5 g ethylene carbonate and 1.5 g water. Finally a pressed part is prepared from the absorbent polymer structure which has been brought into contact with the aqueous solution and the density thereof and the pressure exerted to destroy the pressed part determined.

The properties of the absorbent polymer structures brought into contact with the aqueous solution in examples 5 and 6 as well as in comparison example 9 are summarised in the following Table 2:

TABLE 2

| | Density of pressed part ($kg/cm^3$) | Exerted Pressure (Pascal) |
|---|---|---|
| Example 6 | 486 | 8,795 |
| Example 7 | 474 | 4,575 |
| Comparison Example 9 | 410 | 16,295 |

The results show that the formation of stable agglomerates is significantly restrained by addition of silicic acid sol. By this addition is achieved that the absorbent polymer structure (Pu1) or (Pu2) can be subjected to increased quantities of liquids without the processability being impaired by clumping.

Test Methods

Permeability in the Swollen State (SFC Test)

The determination of the permeability in the swollen state (Saline Flow Conductivity=SFC) is carried out according to a method described in WO 95/22356. Approx. 0.9 g superabsorbent material are weighed into a cylinder with a sieve floor and carefully distributed on the sieve surface. The superabsorber material is left to swell in JAYCO synthetic urine for 1 hour under a pressure of 20 $g/cm^2$. After recording the swell height of the superabsorber, 0.118 M NaCl solution from a levelled storage vessel is allowed to pass through the swollen gel layer under constant hydrostatic pressure. The swollen gel layer is covered with a special sieve cylinder during the measurement, which ensures an equal distribution of the 0.118 M NaCl solution over the gel and constant conditions (measurement temperature 20-25° C.) during the measurement regarding the gel-bed state. The pressure acting on the swollen superabsorber is continually 20 $g/cm^2$. With the aid of a computer and a balance the quantities of liquid which pass through the gel sheet as a function of time are recorded in intervals of 20 seconds within a time period of 10 minutes. The flow rate g/s through the swollen gel layer is determined by means of regressions analysis by extrapolation of the gradient and determination of the centre at the time-point t=0 of the flow quantities within minutes 2-10. The SFC value (K) was given in $cm^3 \cdot s \cdot g^{-1}$ and calculated as follows:

$$K = \frac{F_s(t=0) \cdot L_o}{r \cdot A \cdot \Delta P_1} = \frac{F_s(t=0) \cdot L_o}{139506}$$

where $F_s(t=0)$ is the flow rate in g/s,
$L_o$ the thickness of the gel layer in cm,
r the density of the NaCl solution (1.003 $g/cm^3$),
A the surface of the upper side of the gel layer in the measuring cylinder (28.27 $cm^2$),
$\Delta P$ the hydrostatic pressure exerted on the gel layer (4920 $dyne/cm^2$), and
K the SFC value.

Determination of the Agglomeration Tendency

The tendency of liquid-coated superabsorbers to form agglomerates is determined by an Indiciser of the firm J. R. Johanson Inc. Thus the superabsorber is coated with the secondary cross-linker solution to be investigated and finally 50 g of the powder used in the investigation. The apparatus prepares a pressed part with a height of approx. 2 cm using a defined pressure of 160,000 Pa by means of a press stamp in a hollow metallic cylinder which has an inner diameter of 5.23 cm. This pressed part is finally destroyed again by being passed through a second cylinder which has a diameter of 4.2 cm, and the force necessary therefore is measured.

The invention claimed is:

1. An absorbent polymer structure (Pa), comprising an inner portion as well as an outer portion surrounding the inner portion, wherein the inner portion comprises a crosslinked polymer and the outer portion comprises a crosslinked polymer, wherein the polymer of the outer portion is more strongly cross-linked than the polymer of the inner portion, wherein the polymer of the outer portion is surface crosslinked with an aqueous solution comprising a chemical cross-linker, and an inorganic compound comprising silicic acid, and heating the absorbent polymer structure to a temperature of from about 40 to about 300° C., wherein said inorganic compound is at least partly immobilized in the polymer of the outer portion and wherein the absorbent polymer structure (Pa) has a CRC of at least about 26 g/g and a SFC of at least about $60 \cdot 10^{-7}$ $cm^3 \cdot s \cdot g^{-1}$.

2. The absorbent polymer structure (Pa) according to claim 1, wherein the absorbent polymer structure has an Absorbency against Pressure (AAP) of at least about 18 g/g under a pressure of about 50 $g/cm^2$.

3. The absorbent polymer structure (Pa) according to claim 1, wherein the chemical cross-linker comprises ethylene carbonate and the inorganic compound is a condensate of polysilicic acids.

4. A composite comprising an absorbent polymer structure (Pa) according to claim 1 and a substrate.

5. A process for producing a composite, wherein an absorbent polymer structure (Pa) according to claim 1 and a substrate and optionally an additive are brought into contact with each other.

6. A composite produced by a process according to claim 5.

7. Chemical products, comprising the absorbent polymer structure (Pa) according to claim 1.

8. The absorbent polymer structure (Pa) according to claim 1, wherein the absorbent polymer structure has a CRC from about 26 g/g to about 35 g/g.

9. The absorbent polymer structure (Pa) according to claim 1, wherein the absorbent polymer structure has a SFC from about $60 \cdot 10^{-7}$ cm$^3 \cdot$s$\cdot$g$^{-1}$ to about $150 \cdot 10^{-7}$ cm$^3 \cdot$s$\cdot$g$^{-1}$.

10. A process for producing an absorbent polymer structure (Pa) by treating an outer portion of an untreated absorbent polymer structure (Pu1), comprising the steps of:

bringing the outer portion of the untreated absorbent polymer structure (Pu1) into contact with an aqueous solution comprising at least one chemical cross-linker and at least one inorganic compound in dispersed colloidal form; and heating the absorbent polymer structure, of which the outer portion has been brought into contact with the aqueous solution, at a temperature in the range from about 40 to about 300° C., so that the outer portion of the absorbent polymer structure is more strongly cross-linked compared to the inner portion and the inorganic compound is at least partly immobilized in the outer portion of the absorbent polymer structure and wherein the absorbent polymer structure (Pa) has a CRC of at least about 26 g/g and a SFC of at least about $60 \cdot 10^{-7}$ cm$^3 \cdot$s$\cdot$g$^{-1}$.

11. A process for producing an absorbent polymer structure (Pa) by treating the outer portion of an absorbent polymer structure (Pu2), that has not been treated with an inorganic compound in dispersed colloidal form, comprising the steps of:

bringing the outer portion of the absorbent polymer structure (Pu2) into contact with an aqueous solution comprising at least one chemical cross-linker and at least one inorganic compound in dispersed colloidal form; and heating the absorbent polymer structure, of which the outer portion has been brought into contact with the aqueous solution, at a temperature in the range from about 40 to about 300° C., so that the outer portion of the absorbent polymer structure is more strongly cross-linked compared to the inner portion and the inorganic compound is at least partly immobilized in the outer portion of the absorbent polymer structure and wherein the absorbent polymer structure (Pa) has a CRC of at least about 26 g/g and a SFC of at least about $60 \cdot 10^{-7}$ cm$^3 \cdot$s$\cdot$g$^{-1}$.

12. The process according to claim 1, wherein the absorbent polymer structure (Pu1) is based on:

($\alpha$1) about 20 to about 99.999 wt. % of polymerized, ethylenically unsaturated, acidic group-containing monomers or salts thereof or polymerized, ethylenically unsaturated monomers containing a protonated or a quaternary nitrogen, or mixtures thereof, ($\alpha$2) 0 to about 80 wt. % of polymerized, monoethylenically unsaturated monomers which can be co-polymerized with ($\alpha$1), ($\alpha$3) about 0.001 to about 5 wt. % of one or more cross-linkers, ($\alpha$4) 0 to about 30 wt. % of a water soluble polymer, as well as ($\alpha$5) 0 to about 20 wt. % of one or more additives, wherein the sum of the component weights ($\alpha$1) to ($\alpha$5) amounts to 100 wt. %.

13. The process according to claim 1 wherein the absorbent polymer structure (Pu1) is brought into contact with at most about 20 wt. % of the aqueous solution, based on the weight of the absorbent polymer structure (Pu1).

14. The process according to claim 1 wherein two separate aqueous solutions, of which one contains the chemical cross-linker and the other the inorganic compound in dispersed colloidal form, are brought simultaneously into contact with the absorbent polymer structure (Pu1).

15. The process according to claim 1 wherein at least about 30 wt. % of the inorganic compound in the aqueous solution, with which the outer portion of the absorbent polymer structure (Pu1) is brought into contact, comprises particles with a particle size within a range from about 1 to about 100 nm.

16. The process according to claim 1 wherein the inorganic compound is used in an amount from about 0.001 to about 10 wt. % based on the absorbent polymer structure (Pu1), in the treatment of the outer portion of an absorbent polymer structure (Pu1).

17. The process according to claim 1 wherein particles comprising polysilicic acid are used as inorganic compound.

18. The process according to claim 1 wherein a condensation cross-linker is used as the chemical cross-linker.

* * * * *